United States Patent
Wanezaki et al.

(10) Patent No.: US 7,638,643 B2
(45) Date of Patent: *Dec. 29, 2009

(54) PROCESS FOR PRODUCING SOYBEAN SAPONIN-CONTAINING MATERIAL

(75) Inventors: Satoshi Wanezaki, Izumisano (JP);
Shinichi Tsuzaki, Izumisano (JP);
Hideo Araki, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 837 days.

This patent is subject to a terminal disclaimer.

(21) Appl. No.: 10/507,637

(22) PCT Filed: Mar. 11, 2003

(86) PCT No.: PCT/JP03/02881

§ 371 (c)(1),
(2), (4) Date: Sep. 14, 2004

(87) PCT Pub. No.: WO03/075939

PCT Pub. Date: Sep. 18, 2003

(65) Prior Publication Data

US 2005/0123662 A1    Jun. 9, 2005

(30) Foreign Application Priority Data

Mar. 14, 2002    (JP)    ............ 2002-070048

(51) Int. Cl.
*C11B 1/00*    (2006.01)
(52) U.S. Cl. .......... 554/15; 554/8; 554/9; 554/12
(58) Field of Classification Search ......... 554/8, 554/9, 12, 15
See application file for complete search history.

(56) References Cited

U.S. PATENT DOCUMENTS 5,789,581 A * 8/1998 Matsuura et al. ........... 536/128

6,033,714 A * 3/2000 Gugger et al. .............. 426/634

FOREIGN PATENT DOCUMENTS

| JP | 61-36225 | * | 2/1986 |
| JP | 61-129134 | * | 6/1986 |
| JP | 62-5917 | * | 1/1987 |
| JP | 4-36242 | | 2/1992 |
| JP | 04-36242 | * | 2/1995 |

OTHER PUBLICATIONS

Makoto Shimoyamada et al., "Solubilities of Soybean Saponins and Their Solubilization with a Bisdesmoside Saponin", Nippon Shokuhin Kogyo Gakkaishi, vol. 40, No. 3, pp. 210 to 213, 1993.
Makoto Shimoyamada et al., "Partition of Soybean Saponins between Butanol and Water", Food Sci. Technol. Int., vol. 1, No. 2, pp. 112 to 114, 1995.
Aaron P. Griffith et al., "Improved methods for the extraction and analysis of isoflavones from soy-containing food and nutritional supplements by reversed-phase high-performance liquid chromatography and liquid chromatography-mass spectrometry", J. Chromatography A, vol. 913, pp. 397 to 413, 2001.
Full English translation of JP 61-36225 published Feb. 20, 1986.
Full English translation of JP 4-36242 published Feb. 6, 1992.

* cited by examiner

*Primary Examiner*—Deborah D Carr
(74) *Attorney, Agent, or Firm*—Wenderoth, Lind & Ponack, L.L.P.

(57) ABSTRACT

It is intended to easily separate saponins from isoflavones extracted from starting soybeans thereby giving highly pure saponins at a high yield on an industrial scale. Saponins can be highly efficiently separated from isoflavones by performing multistage extraction under mild conditions such that malonyl isoflavone glycoside, from among isoflavones contained in the starting soybeans, is not converted into isoflavone glycoside, acetyl isoflavone glycoside or isoflavone aglycon. Thus, highly pure saponins can be obtained at a high yield on an industrial scale.

3 Claims, No Drawings

PROCESS FOR PRODUCING SOYBEAN SAPONIN-CONTAINING MATERIAL

TECHNICAL FIELD

The present invention relates to a soybean saponin-containing material and a process for producing the same.

BACKGROUND ART

Soybean saponins (hereinafter, simply noted as "saponins") are a generic name of saponins contained in starting soybeans and are contained in soybean hypocotyls in an amount of about 2 to 4% by weight. Saponins are classified into group A saponin, i.e., bisdesmoside saponin, wherein an aglycone skeleton is "soyasapogenol A" and sugar chains are attached to C-3 position and C-22 position of the aglycone through ether bonds; group B saponin, i.e., monodesmoside saponin, wherein an aglycone skeleton is "soyasapogenol B" and a sugar chain is attached to C-3 position of the aglycone through ether bond; and the like. In addition, saponin, wherein a moiety of a sugar chain is acetylated is also reported (Kitagawa et al, Chem. Phrm. Bull, 33, (1985)).

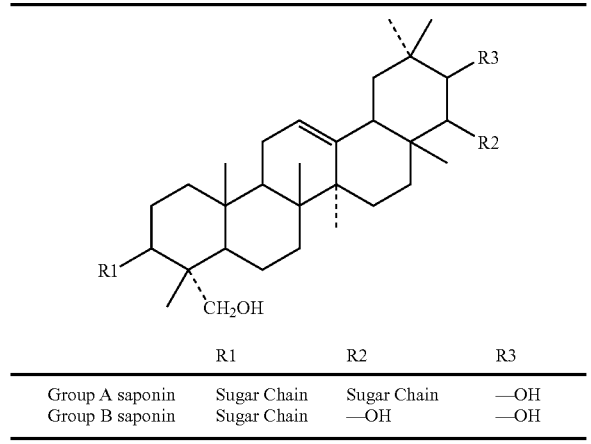

| | R1 | R2 | R3 |
|---|---|---|---|
| Group A saponin | Sugar Chain | Sugar Chain | —OH |
| Group B saponin | Sugar Chain | —OH | —OH |

On the other hand, isoflavones are contained in starting soybeans as trace components other than saponins, and contained in soybean hypocotyls in an amount of about 1 to 2% by weight. Isoflavones are generic name for isoflavone aglycone whose aglycone skeleton is daidzein, glycitein or genistein; isoflavone glycoside, wherein a sugar chain is attached at position 6 of the isoflavone aglycone; and further acetyl isoflavone glycoside or malonyl isoflavone glycoside, wherein its sugar chain has an acetyl group (—$COCH_3$) or a malonyl group (—$COCH_2COOH$) as a functional group.

Saponins are said to have a variety of physiological activities such as anti-obesity activity, antioxidant activity, and an immunity activation activity. Then, when a material containing saponins at a high concentration is available, the material can be utilized by simply adding it to various foods and drinks.

Conventionally, in order to obtain a material containing saponins at a high concentration from starting soybeans such as whole soybeans, defatted soybeans, soybean hypocotyls, and the like, it has been known that appropriate separation of saponins from isoflavones is important (JP 62-5917 A and JP 61-129134 A). Hence, as described in these gazettes, these processes require carrying out purification by gel filtration such as LH-20, or the like, or partition chromatography after carrying out first stage production steps involving extraction with a solvent such as a lower alcohol or acetone, adsorption of the resultant extract with a synthetic adsorption resin such as HP-20 and XAD-2 or activated carbon, washing the absorbed extract with a low concentration of a lower alcohol (10 to 40% by volume) and then elution of a fraction containing saponins with a high concentration of a lower alcohol (70 to 80% by volume).

However, in order to obtain a highly pure saponin fraction in the above-described processes, the final purifying step by means of gel filtration or partition chromatography is required and a multi-stage purifying step is essential. Hence, a yield of saponins is as low as about 1 to 2%. Indeed, for example, the yield of saponins disclosed in Example 1 of JP 62-5917 A from starting soybeans is 1.38%. This is problematic from the viewpoints of facility costs and production efficiency for industrially putting such a process into practice. On the other hand, in order to extract saponins with a solvent at a high yield, conventionally, the extraction is carried out at a high temperature. However, even when such extraction is carried out, a material containing saponins which satisfies requirements of high purity and high yield without complicated operation cannot be obtained.

Thus, an object of the present invention is to facilitate separation of saponins from isoflavones extracted from starting soybeans to obtain a highly pure saponin-containing material at a high yield on an industrial scale.

DISCLOSURE OF THE INVENTION

Regarding the above problem, the present inventors have studied extraction conditions to improve purity and yield of saponins. That is, when the present inventors have studied by raising an extraction temperature, or changing a pH, a yield of saponins can be improved under high temperature conditions, but at the same time solid materials other than saponins are also extracted, which conversely causes a decrease in purity of saponins. Therefore, these conditions require purification operation of two complicated stages as in a conventional technique, and thus resulting in a decrease in a yield. Hence, we have decided to investigate another process.

Then, we have studied intensively to obtain a highly concentrated saponin-containing material at a high yield by means of simple operation without carrying out multi-stage purification operation, and have obtained the following findings.

(1) Hydrophobicities of saponins are particularly close to those of isoflavone glycoside, acetyl isoflavone glycoside, and isoflavone aglycone, among isoflavones. Therefore, it is difficult to separate them by utilizing these properties.

(2) Among isoflavones, malonyl isoflavone glycoside has a dissociation group and thus has a relatively high polarity. Therefore, malonyl isoflavone glycoside can be easily separated from saponins with an adsorbent.

(3) In a natural state, soybeans contain a largest amount of malonyl isoflavone glycoside. However, malonyl isoflavone glycoside is unstable to heat and is easily converted into isoflavone glycoside, acetyl isoflavone glycoside, or isoflavone aglycone by heating.

From the above findings, when multi-stage extraction is carried out under mild conditions at which conversion of malonyl isoflavone glycoside in starting soybeans into isoflavone glycoside, acetyl isoflavone glycoside, or isoflavone aglycone is avoided, saponins can be separated from isoflavones extremely efficiently only by subsequent one-stage purification step, i.e., treatment with an adsorbent to obtain highly pure saponins at a high yield, which leads to a finding of a simple and easy process for producing a saponin-containing material having an extremely high purity at a high yield on an industrial scale. Thus, the present invention has been completed.

That is, the present invention discloses the following:

1. A process for producing a soybean saponin-containing material which comprises preparing a water-containing polar organic solvent extract satisfying the following conditions (a) and (b) from starting soybeans:
    (a) a content of malonyl isoflavone glycoside being 25% by weight or more based on the total amount of isoflavones in said extract, and
    (b) an extraction ratio of soybean saponins from said starting soybeans being 60% by weight or more;
2. The process for producing a soybean saponin-containing material according to the above 1, wherein said starting soybeans are raw soybean hypocotyls;
3. The process for producing a soybean saponin-containing material according to the above 1 or 2, wherein a water content of said water-containing polar organic solvent is from 20 to 85% by volume;
4. The process for producing a soybean saponin-containing material according to any one of the above 1 to 3, wherein extraction is carried out at a temperature of 10 to 72° C.;
5. The process for producing a soybean saponin-containing material according to any one of the above 1 to 4, wherein extraction is carried out in a multi-stage manner;
6. A process for producing a soybean saponin-containing material which comprises purifying the water-containing polar organic solvent extract prepared by the process according to any one of the above 1 to 5 by treatment with an adsorbent;
7. A process for producing a soybean saponin-containing material which comprises subjecting the water-containing polar organic solvent extract prepared by the process according to any one of the above 1 to 5 to treatment with an adsorbent; eluting a soybean isoflavone-containing fraction with a water-containing polar solvent having a water content of 65 to 90% by volume; and then eluting a soybean saponin-containing fraction with a water-containing polar solvent having a water content of 5 to 40% by volume;
8. A soybean saponin-containing material obtained by the process according to the above 7.

BEST MODE FOR CARRYING OUT THE INVENTION

Hereinafter, the present invention will be illustrated in detail.

The present invention is characterized in that, in steps for preparing a saponin-containing extract (hereinafter, noted as a "water-containing polar organic solvent extract") from starting soybeans with a water-containing polar organic solvent, the extraction is carried out such that a content of malonyl isoflavone glycoside is 25% by weight or more, preferably 40% by weight or more, more preferably 50% by weight or more based on the total amount of isoflavones in the extract, and an extraction ratio of saponins in the water-containing polar organic solvent is 60% by weight or more, preferably 70% by weight or more, more preferably 80% or more. When the extraction is carried out under these conditions, highly pure saponins can be obtained at a high yield on an industrial scale. For obtaining a water-containing polar organic solvent extract which meets these conditions, production conditions such as starting soybeans, a kind and a water content of the water-containing polar organic solvent, an extraction temperature, an extraction pH, and an extraction method are appropriately combined. Hereinafter, a preferred aspect for obtaining the water-containing polar organic solvent extract that satisfies the above conditions will be illustrated.

[Process for Preparing Water-Containing Polar Organic Solvent Extract]

(Starting Soybeans)

In the present invention, as a raw material for extracting saponins therefrom, saponin-containing starting soybeans such as whole soybeans, dehulled soybeans, dehulled and hypocotyl-removed soybeans, defatted soybeans, soybean hypocotyls, or the like can be used. In particular, soybean hypocotyls having a relatively high saponin content (about 2 to 4% by weight) as well as a high content of group A saponin which is said to have particularly strong antioxidant activity among saponins (Ohminami et al, Proc. Symp. WAKAN-YAKU, 14, 157-162 (1981)) is preferably used from the viewpoint of a yield. In addition, soybean processed products such as soybean protein isolate, "okara (insoluble residue from soybean milk production, also known as soy pulp)", and tofu can also be used. As soybean hypocotyls, those having less hulls and highly pure hypocotyls are suitable.

Soybean hypocotyls may also be subjected to pre-treatment such as dry heating or wet heating to improve flavor thereof and inactivate trypsin inhibitor. However, when treatment is carried out to such extent that malonyl isoflavone glycoside is converted into isoflavone glycoside and acetyl isoflavone glycoside, separation efficiency in the purification step after extraction can be adversely affected. Therefore, raw soybean hypocotyls are preferably used. When pre-treatment is carried out, mild treatment wherein conversion of malonyl isoflavone glycoside is minimized is preferred.

Examples of the isoflavone compositions of raw soybean hypocotyls and soybean hypocotyls subjected to dry heating are shown in Table 1. In these examples, malonyl isoflavone glycoside in soybean hypocotyls subjected to dry heating (roasting) is mostly converted into isoflavone glycoside or acetyl isoflavone glycoside, and therefore dry heating to such extent is not preferred.

TABLE 1

| Isoflavone composition | Raw hypocotyls | Dry heated hypocotyls |
| --- | --- | --- |
| Isoflavone glycosides | | |
| Daidzin | 10.9 | 25.5 |
| Genistin | 2.7 | 6.7 |
| Glycitin | 8.7 | 19.5 |
| Malonyl isoflavone glycosides | | |
| Malonyl daidzin | 48.7 | 0.1 |
| Malonyl genistin | 9.7 | 0.1 |
| Malonyl glycitin | 18.2 | 0.3 |
| Acetyl isoflavone glycosides | | |
| Acetyl daidzin | 0.2 | 21.8 |
| Acetyl genistin | 0.0 | 7.5 |
| Acetyl glycitin | 0.2 | 15.3 |
| Isoflavone aglycons | | |
| Daidzein | 0.4 | 0.6 |
| Genistein | 0.0 | 0.2 |
| Glycitein | 0.3 | 2.4 |
| Total | 100.0 | 100.0 |

(Extraction Solvent)

As a solvent for extracting saponins from starting soybeans, a water-containing polar organic solvent, i.e., an organic solvent miscible with water which contains water in a desired ratio is used. Examples of a hydrophilic organic solvent include lower alcohols such as methanol, ethanol, propanol, etc.; acetone; and the like. In particular, ethanol is preferably used. It is advisable to avoid the use of non-polar organic solvents such as ether, chloroform, hexane, etc., because they have inferior extraction efficiencies of glycoside components such as isoflavones and saponins.

A water content of the water-containing polar organic solvent varies depending upon the kind of a polar organic solvent and may be selected so that highly pure saponins can be extracted at a high yield. The water content is preferably 20 to 85% by volume, more preferably from 25 to 70% by volume, still more preferably from 25 to 60% by volume. When the water content is too small, a saponin extraction ratio is extremely lowered. On the other hand, when it is too large, saponins cannot be separated from isoflavones easily and purity of saponins tends to be lowered due to an increase in a ratio of isoflavone aglycons formed by decomposition of isoflavone glycoside and its malonyl and acetyl derivatives, perhaps, because of β-glycosidase present in soybean hypocotyls.

The amount of the water-containing polar organic solvent relative to starting soybeans to be used for each extraction is not specifically limited, and varies depending upon the kind of a solvent. From an economical viewpoint, preferably, the amount is 3 to 10 L per 1 kg of starting soybeans.

(Extraction Temperature)

Extraction of saponins from starting soybeans is preferably carried out at such a temperature that malonyl isoflavone glycoside is hardly converted into isoflavone glycoside and acetyl isoflavone glycoside, or lower, more preferably from 10 to 72° C., still more preferably from 20 to 65° C. When the extraction temperature is too low, saponins cannot be extracted easily and a yield tends to be lowered. On the other hand, when the extraction temperature is too high, saponins cannot be separated easily and purity of saponins tends to be lowered due to an increase in isoflavone glycoside and acetyl isoflavone formed by hydrolysis or decarboxylation of the malonyl group of malonyl isoflavone glycoside.

(Extraction pH)

The water-containing organic solvent is preferably pH 4 to 9, more preferably 5 to 8. When the pH is too low, saponins in the resultant extract tends to precipitate depending upon a water content of the water-containing organic solvent, thereby making the subsequent fractionation step troublesome. On the other hand, when the pH is too high, separation efficiency of saponins from isoflavones tends to be lowered because malonyl isoflavone glycoside is easily converted into isoflavone glycoside.

(Extraction Method)

An extraction method may be selected so that an extraction ratio of saponins from starting soybeans into the water-containing polar organic solvent extract is 60% by weight or more, more preferably 70% by weight or more, still more preferably 80% by weight or more. For example, it is preferable to select a multi-stage extraction method wherein at least two or more-stage extraction is carried out. In this procedure, extraction may be carried out plural times in one extraction vessel (tank) (butch-wise), or once or more in each of plural tanks connected to each other in series. Further, it is also possible to arrange one or more tanks in parallel to each of tanks connected to each other in series. In addition to a multi-stage extraction method, a counterflow continuous-extraction method or the like can also be employed. The methods illustrated above can be selected by taking into account the space in a production site, costs, and the like. On the other hand, in case that the extraction is carried out only once, an extraction ratio of saponins from starting soybean cannot be increased easily and a yield tends to be lowered.

In the water-containing polar organic solvent extract obtained from the above aspect, saponins are recovered from starting soybeans at a high yield (60% by weight or more), and the ratio of malonyl isoflavone glycoside in total isoflavones is high (25% by weight or more). The extract satisfying such conditions makes the subsequent separation of saponins from isoflavones and purification of saponins extremely easy. On the other hand, when the extraction is not carried out under mild conditions, and the content of malonyl isoflavone glycoside becomes less than 25% by weight based on the total isoflavones in the resultant water-containing polar organic solvent extract, and conversely the content of isoflavone glycoside, acetyl isoflavone glycoside, and isoflavone aglycone is increased to 75% by weight or more, the separation of saponin-containing fraction therefrom becomes difficult, which extremely lowers purity of saponins, and requires a complicated purification step.

[Purification Method of Saponin-Containing Fraction]

Then, an isoflavone fraction can be extremely easily removed from the resultant water-containing polar organic solvent extract by means of a conventional purification means to obtain a highly pure saponin fraction at a high yield. Hereinafter, a preferred aspect of the purification step will be illustrated.

(Treatment of Extract with Adsorbent)

The resultant water-containing polar organic solvent extract is first treated with an adsorbent. That is, saponins are adsorbed on an adsorption resin or the like. As the adsorption resin, a well-known resin can be used. Preferred examples to be used include a synthetic adsorption resin such as a porous styrene-divinylbenzene type resin, for example, HP-20 (manufactured by Mitsubishi Chemical Corporation), SP-825 (manufactured by Mitsubishi Chemical Corporation), Amberlite XAD-2 or XAD-4 (manufactured by Rohm and Haas Company), Duolite S-861 or S-862 (manufactured by Sumitomo Chemical Co. Ltd.), and the like. This procedure may be carried out by introducing the resin into a tank in batch-wise, or can be performed by packing the resin into a column.

(Elution of Isoflavone-Containing Fraction)

Then, a fraction highly containing saponins adsorbed on the resin is eluted to purify a saponin-containing fraction. Specifically, the purification can be carried out by the following method.

Components other than saponins, e.g., isoflavones and the like are selectively removed from the fraction adsorbed on the resin with a water-containing polar organic solvent having a high water content. The water content of the water-containing polar organic solvent is preferably from 65 to 90% by volume. When the water content is too high, a large amount of a solvent is required to elute an isoflavone fraction. On the other hand, when the water content is too low, saponins as well as isoflavones are eluted simultaneously, which lowers the separation efficiency, thereby lowering the purity of saponins.

(Elution of Saponin-Containing Fraction)

Then, a saponin-containing fraction is selectively eluted with a water-containing polar organic solvent having a low water content and recovered. The water content of the water-containing polar organic solvent is preferably 5 to 40% by volume, more preferably 10 to 35% by volume. When the water content is too high, not only a large amount of a solvent is required to elute a saponin-containing fraction, but also saponins cannot be recovered completely, thereby causing a low yield. On the other hand, when the water content is too low, efficiency of elution is lowered, thereby increasing costs.

(Processing of Saponin-Containing Fraction)

An eluent of the resultant saponin-containing fraction as such can be processed into a concentrated solution, or processed into powders or granules to obtain the "soybean saponin-containing material."

The resultant soybean saponin-containing material has high purity such as that having a saponin content of 40% by weight or more, preferably 50% by weight based on the solid matter. In addition, a yield from starting soybeans is high. Thus, the material is a product obtained by a process of remarkably high production efficiency.

In case of using soybean hypocotyls as starting soybeans, group A saponin is contained in an amount of 60% or more in the resultant saponin-containing fraction. Therefore, such a product is very useful as the saponin-containing material having higher antioxidant activity.

(Application to Foods, Etc.)

By ingestion of the resultant soybean saponin-containing material, anti-obesity effect, antioxidant effect, lever damage-improving effect, serum lipid-improving effect, and the like are also expected. Then, the material can be utilized for tablets, confectionary, drinks, other health drinks and foods, medical supplies, cosmetics, and the like.

In the present invention, saponins were determined by thin layer chromatography. And, isoflavones were determined according to Soybean Isoflavone Food Specification Standard Analysis Method of Japan Health Food & Nutrition Food Association. Hereinafter, each method will be illustrated.

(Method for Determination of Saponins)

A sample was precisely weighed, and methanol was added thereto. After stirring and extracting for one hour, the mixture was centrifuged to obtain an extract. This was repeated again and the combined extract was made up to a given volume. This was applied to thin layer chromatography (TLC), and then the Rf values of the sample were compared with those of saponin standards to confirm the spots of saponins. By using a standard straight line prepared with saponin standards in advance, the area integration values of the spots were measured to calculate the amount of saponins. Table 2 shows the conditions of thin layer chromatography.

TABLE 2

| TLC Conditions | |
| --- | --- |
| TCL plate | Silica gel 60F245 (0.25 mm thick, manufactured by Merck Corp.) |
| Developing solvent | chloroform-methanol-water mixed solution (65:25:10, v/v/v lower layer) |
| Development | 18 cm |
| Detection | Ten (10)% sulfuric acid solution was sprayed, and then heated at 105° C. for 15 min. |

(Method for Determining an Isoflavone)

A sample containing 1 to 10 mg of soybean isoflavones was precisely weighed, and 25 mL of 70% by volume ethanol was added thereto. After stirring and extracting at room temperature for 30 minutes, the mixture was centrifuged to obtain an extract. Further, the residue was subjected to similar extraction operation twice. The resultant three extracts were combined, made up to 100 mL with 70% by volume ethanol, and then filtrated with a 0.45 μm PVDF filter to obtain a test solution. The identification testing of soybean isoflavones was carried out by using 12 kinds of the standards, i.e., daidzin, genistin, glycitin, daidzein, genistein, glycitein, malonyl daidzin, malonyl genistin, malonyl glycitin, acetyl daidzin, acetyl genistin, and acetyl glycitin (Wako Pure Chemical Industries, Ltd.) to confirm peaks having almost the same retention times. The determination testing was carried out by determining isoflavone concentrations (in terms of daidzin values) of 12 kinds with the daidzin standard and true isoflavone concentrations were calculated by multiplying the determination coefficients below.

Determination coefficients of isoflavones: daidzin (1.000), genistin (0.814), glycitin (1.090), malonyl daidzin (1.444), malonyl genistin (1.095), malonyl glycitin (1.351), acetyl daidzin (1.094), acetyl genistin (1.064), acetyl glycitin (1.197), daidzein (0.583), genistein (0.528), glycitein (0.740).

The amount of isoflavones was calculated from the total of respective isoflavone concentrations.

HPLC conditions of the test solutions and the standard solutions are shown in Table 3.

TABLE 3

| HPLC Conditions | | |
| --- | --- | --- |
| Column | YMC-Pack ODS-AM-303 (4.6 × 250 mm) | |
| Mobile phase | A solution | acetonitrile:water:acetic acid = 15:85:0.1 (v/v/v) |
| | B solution | acetonitrile:water:acetic acid = 35:65:0.1 (v/v/v) |
| | A solution to B solution | linear concentration gradient (for 50 min) |
| Flow rate | 1.0 ml/min | |
| Temperature | 25° C. | |
| Detection | UV 254 nm | |
| Injection amount | 10 μL | |

EXAMPLES

The following Examples further illustrate the present invention in detail but are not to be construed to limit the technical scope thereof. In the Examples, all "percents" are by weight unless otherwise stated.

Example 1

To 500 g of raw soybean hypocotyls was added 2.0 L of water-containing ethanol having a water content of 25% by volume and the resultant mixture was stirred and extracted at 40° C. After separation of the extract by filtration, again thereto was added 2.0 L of water-containing ethanol having a water content of 25% by volume, and the resultant mixture was similarly extracted. The resultant two extracts were combined (the resultant extract was referred to as a "water-containing polar organic solvent extraction solution"). The extract was condensed at 40° C. under reduced pressure.

The extract thus obtained was dissolved in water and the resulting solution was applied to a column (100 ml) packed with a porous styrene-divinylbenzene type synthetic adsorption resin Diaion HP-20 (manufactured by Mitsubishi Chemical Corporation) at SV2.

Then, the column was washed with water-containing ethanol having a water content of 80% by volume and further eluted with water-containing ethanol having a water content of 20% by volume to obtain a saponin fraction. This fraction was condensed at 40° C. under reduced pressure to obtain a saponin-containing material in the form of a dry powder.

Example 2

According to the same manner as that described in Example 1, a saponin-containing material was obtained except that extraction of raw soybean hypocotyls with water-containing ethanol was carried out at 70° C.

Example 3

According to the same manner as that described in Example 1, a saponin-containing material was obtained except that extraction of raw soybean hypocotyls with water-containing ethanol was carried out at 15° C.

Comparative Example 1

According to the same manner as that described in Example 1, a saponin-containing material was obtained except that the extraction was carried out only once.

Comparative Example 2

According to the same manner as that described in Example 1, a saponin-containing material was obtained except that the starting soybeans were changed to roasted soybean hypocotyls.

Table 4 shows saponin yields from starting soybeans (% by weight), and abundance ratios (%) of malonyl isoflavone glycoside (Mal-iso), acetyl isoflavone glycosides (Ac-iso), isoflavone glycosides (Iso) and isoflavone aglycons (Agl) by taking the total amount of isoflavones in each extract as 100% of the respective water-containing polar organic solvent extracts obtained in Examples 1 to 3 and Comparative Examples 1 and 2; as well as saponin contents (% by weight), isoflavone contents (% by weight) and saponin yields from starting soybeans of the respective saponin-containing materials obtained by treatment with the adsorbent.

result, in the saponin-containing material obtained, the saponin content was extremely high (60%), and the yield was also high (72%). On the other hand, the isofravone content was only 2% by weight, indicating that extremely appropriate separation of isoflavones and saponins from the extract was accomplished, though, usually, separation of isoflavones and saponins was difficult. Further, 67% of saponins contained in the saponin-containing material in Example 1 was group A saponin.

In Example 2, the saponin yield of the saponin-containing material was extremely high (73% by weight) as in Example 1, but the abundance ratio of malonyl isoflavone glycoside of the extract was 25.3%, thereby lowering the saponin content of the saponin-containing material as compared with that for Example 1. Nevertheless, the saponin content was 40% by weight and this was a satisfactory content. This lowering of the saponin content to 25.3 is considered to be due to the extraction temperature of 70° C., which causes lowering of the abundance ratio of malonyl isoflavone glycoside in the extract as compared with that of Example 1, while increasing the abundance ratios of acetyl isoflavone glycoside and isoflavone glycoside.

On the other hand, in Comparative Example 1, although the saponin content of the resultant saponin-containing material was 48% by weight, the saponin yield of the extract was 42% by weight, probably, due to the only once extraction. As a result, the saponin yield of the saponin-containing material was as low as 32% by weight, thereby lowering the production efficiency.

In Comparative Example 2, although the saponin yield of the saponin-containing material was high (78% by weight), while the saponin content of the saponin-containing material

TABLE 4

|  | Example 1 | Example 2 | Example 3 | Comparative Example 1 | Comparative Example 2 |
| --- | --- | --- | --- | --- | --- |
| (Extraction conditions) | | | | | |
| Starting Soybeans | raw hypocotyls | raw hypocotyls | raw hypocotyls | raw hypocotyls | Roasted hypocotyls |
| Extraction temperature | 40° C. | 70° C. | 15° C. | 40° C. | 40° C. |
| Number of extractions | 2 | 2 | 2 | 1 | 2 |
| Water content (Water-containing polar organic solvent extract) | 25% | 25% | 25% | 25% | 25% |
| Saponin yield | 85% | 88% | 68% | 42% | 82% |
| Isoflavone abundance ratio (%) | | | | | |
| Mal-iso | 54.2 | 25.3 | 59.6 | 47.0 | 0.5 |
| Ac-iso | 4.3 | 6.2 | 4.3 | 2.3 | 45.0 |
| Iso | 39.5 | 68.5 | 33.5 | 49.2 | 51.0 |
| Agl | 2.0 | 0.0 | 2.6 | 1.5 | 3.5 |
| (Saponin-containing material) | | | | | |
| Saponin content | 60% | 40% | 56% | 48% | 25% |
| Isoflavone content | 2% | 8% | 6% | 3% | 18% |
| Saponin yield | 72% | 73% | 56% | 32% | 78% |

As seen from Table 4, in Example 1 the saponin yield of the extract was as extremely high as 85% and the abundance ratio of malonyl isoflavone glycoside was as high as 54.2%. As a was as extremely low as 25% by weight. Further, the content of isoflavones was 18% by weight. This showed that the fractionation of isoflavones and saponins was not appropriately carried out. This is considered to be caused by the use of dry heated (roasted) soybean hypocotyls as starting soybeans, thereby causing conversion of heat unstable malonyl isoflavone glycoside into acetyl isoflavone glycoside.

Consequently, it has been found that the higher an abundance ratio of malonyl isoflavone glycosides of an extract is, the better saponins are fractionated. Further, it has been found that, as the abundance ratio of malonyl isoflavone glycosides is decreased and as the abundance ratios of acetyl isoflavone glycoside and isoflavone glycoside are increased, elution patterns of isoflavones and saponins during the separation with an adsorption resin are overlapped with each other, making it difficult to separate isoflavones from saponins.

Experiment 1

Study of Water Content of Water-Containing Polar Organic Solvent

In order to study the influence of an water content of a water-containing polar organic solvent during extraction, variations of contents of saponins and isoflavones in extracts obtained according to the same manner as that in described Example 1 were examined by changing water contents of extraction solvents as shown in Table 5.

TABLE 5

| (Isoflavone | Water content (%) | | | | | | |
| --- | --- | --- | --- | --- | --- | --- | --- |
| | 0 | 10 | 30 | 50 | 60 | 80 | 90 |
| | Saponin yield (%) | | | | | | |
| abundance ratio) | 10 | 38 | 86 | 82 | 82 | 76 | 63 |
| Mal-iso | 28.6 | 45.3 | 55.3 | 59.6 | 60.3 | 65.3 | 18.0 |
| Ac-iso | 0.0 | 0.0 | 3.3 | 4.1 | 6.3 | 2.1 | 6.3 |
| Iso | 64.3 | 46.6 | 36.3 | 33.0 | 31.1 | 20.6 | 23.7 |
| Agl | 7.1 | 8.1 | 5.1 | 3.3 | 2.3 | 12.0 | 52.0 |

As seen from Table 5, when the water content was 0% or 10%, the recovery rate of saponins was inferior. Further, the abundance ratio of malonyl isoflavone glycoside tended to be decreased. When the water content was 90%, the saponin recovery rate was high, but the abundance ratios of isoflavone glycoside and malonyl isoflavone glycoside were extremely lowered. It is considered that this is due to decomposition of glycosides by the action of β-glucosidase to form aglycons. As a result, from the viewpoints of the saponin recovery rate and the abundance ratio of malonyl isoflavone glycoside, the water content of a water-containing polar organic solvent to be used for extraction is preferably 20 to 85% by volume, more preferably 25 to 75% by volume.

Experiment 2

Influence of pH of Extract

In order to study the influence of pH during extraction, the saponin recovery rate and the isoflavone abundance ratio in an extract obtained according to the same manner as that described in Example 1 were measured by changing the pH of a water-containing polar organic solvent as shown in Table 6. The pH was adjusted by using hydrochloric acid and a sodium hydroxide solution.

TABLE 6

| | Example 1 | Comparative Example 3 | Comparative Example 4 |
| --- | --- | --- | --- |
| Extraction solvent pH | 6.5 | 3.5 | 11.0 |
| Saponin yield (%) | 85 | <u>43</u> | 68 |
| Isoflavone abundance ratio (%) | | | |

TABLE 6-continued

| | Example 1 | Comparative Example 3 | Comparative Example 4 |
| --- | --- | --- | --- |
| Mal-iso | 54.2 | 37.9 | <u>2.3</u> |
| Ac-iso | 4.3 | 2.3 | 4.1 |
| Iso | 39.5 | 49.2 | 82.8 |
| Agl | 2.0 | 10.6 | 8.8 |

As shown in Table 6, in Comparative Example 3, a precipitate was formed during extraction and the saponin recovery rate was extremely lowered. Further, in recovery of the extract, the separation was inferior and the operation efficiency was extremely decreased. This is considered to be caused by lowering of solubility of saponins due to lowering of pH and further by lowering of the saponin recovery rate due to co-precipitation of saponins consequent to formation of a protein precipitate.

In Comparative Example 4, the abundance ratio of malonyl isoflavone glycoside in the extract was extremely lowered. This is considered to be caused by instability of malonyl isoflavone glycoside under alkaline conditions. The malonyl group is easily dissociated, thereby converting malonyl isoflavone into the glycoside. Then, elution patterns of isoflavones and saponins are overlapped during the separation with an adsorbing resin, which makes it difficult to separate the isoflavones and the saponins. Thus, it has been judged that a highly pure soybean saponin-containing material cannot be obtained.

As a result, in view of the saponin content and recovery rate, it is considered that the pH of a water-containing polar organic solvent is preferably 4 to 9, which is nearly neutral, more preferably 5 to 8.

INDUSTRIAL APPLICABILITY

According to the present invention, it is possible to obtain a highly pure saponin-containing material at a high yield on an industrial scale only by such one purification step as treatment with an adsorbent without a subsequent multi-stage purification step such as gel filtration and partition chromatography from a saponin-containing solution extracted from starting soybeans, thereby providing a process for producing a saponin-containing material having extremely high production efficiency. Therefore, the present invention is extremely useful in industrial fields such as foods, cosmetics, and medical products.

The invention claimed is:

1. A process for producing a soybean saponin-containing material which comprises the steps of:
   extracting raw soybean hypocotyls, without pre-treatment thereof, with a water-containing polar solvent having a water content of 20 to 85% by volume at 10 to 72° C. by multi-stage extraction to prepare a water-containing polar organic solvent extract satisfying the following conditions (a) and (b):
   (a) a content of malonyl isoflavone glycoside being 25% by weight or more based on the total amount of isoflavones in said extract, and
   (b) an extraction ratio of soybean saponins from said raw soybean hypocotyls being 60% by weight or more;
   purifying the water-containing polar organic solvent extract only by treatment with an adsorbent;

eluting a soybean isoflavone-containing fraction with a water-containing polar solvent having a water content of 65 to 90% by volume; and then eluting a soybean saponin-containing fraction with a water-containing polar solvent having a water content of 5 to 40% by volume to obtain the soybean saponin-containing material.

2. The process according to claim 1, wherein 60% or more of saponins in the saponin-containing material is group A saponin.

3. A method for separation of soybean saponins from isoflavones which comprises the steps of:

extracting raw soybean hypocotyls, without pre-treatment thereof, with a water-containing polar solvent having a water content of 20 to 85% by volume at 10 to 72° C. by multi-stage extraction to prepare a water-containing polar organic solvent extract satisfying the following conditions (a) and (b):

(a) a content of malonyl isoflavone glycoside being 25% by weight or more based on the total amount of isoflavones in said extract, and (b) an extraction ratio of soybean saponins from said raw soybean hypocotyls being 60% by weight or more;

purifying the water-containing polar organic solvent extract only by treatment with an adsorbent;

eluting a soybean isoflavone-containing fraction with a water-containing polar solvent having a water content of 65 to 90% by volume; and then eluting a soybean saponin-containing fraction with a water-containing polar solvent having a water content of 5 to 40% by volume to obtain the soybean saponin-containing material.

* * * * *